United States Patent [19]

Jirousek et al.

[11] Patent Number: 5,723,456
[45] Date of Patent: Mar. 3, 1998

[54] THERAPEUTIC TREATMENT FOR CARDIOVASCULAR DISEASES

[75] Inventors: Michael R. Jirousek, Indianapolis; William Francis Heath, Jr., Fishers; Douglas Kirk Ways; Lawrence E. Stramm, both of Indianapolis, all of Ind.

[73] Assignee: Eli Lilly & Company, Indianapolis, Ind.

[21] Appl. No.: 662,623

[22] Filed: Jun. 13, 1996

Related U.S. Application Data

[60] Continuation-in-part of Ser. No. 643,706, May 6, 1996, which is a division of Ser. No. 413,735, Mar. 30, 1995, Pat. No. 5,624,949, which is a continuation-in-part of Ser. No. 316,973, Oct. 3, 1994, abandoned, which is a continuation-in-part of Ser. No. 163,060, Dec. 7, 1993, abandoned.

[51] Int. Cl.$^6$ .................... A61K 31/55; C07D 487/22
[52] U.S. Cl. .................... 514/183; 514/410; 514/450; 514/459; 540/470; 540/467; 540/472; 540/474
[58] Field of Search .................... 514/183, 410, 514/450, 459

[56] References Cited

U.S. PATENT DOCUMENTS

| | | | |
|---|---|---|---|
| 4,785,085 | 11/1988 | Kaneko | 536/23 |
| 4,808,613 | 2/1989 | Kaneko | 514/42 |
| 4,877,776 | 10/1989 | Murakata | 514/43 |
| 4,923,986 | 5/1990 | Murakata | 540/545 |
| 5,043,335 | 8/1991 | Kleinschroth | 14/211 |
| 5,057,614 | 10/1991 | Davis et al. | 548/466 |
| 5,292,747 | 3/1994 | Davis et al. | 514/285 |
| 5,380,746 | 1/1995 | Barth et al. | 514/414 |
| 5,438,050 | 8/1995 | Kleinschroth et al. | 514/183 |

FOREIGN PATENT DOCUMENTS

| | | |
|---|---|---|
| 3914764 | 8/1990 | Denmark. |
| 0 269 025 | 1/1988 | European Pat. Off.. |
| 0 328 000 | 2/1989 | European Pat. Off.. |
| 0 384 349 | 2/1990 | European Pat. Off.. |
| 0 397 060 | 5/1990 | European Pat. Off.. |
| 0 434 057 | 12/1990 | European Pat. Off.. |
| 0 470 490 | 7/1991 | European Pat. Off.. |
| 0 508 792 | 4/1992 | European Pat. Off.. |
| 0 540 956 | 10/1992 | European Pat. Off.. |
| 0 624 586 | 5/1994 | European Pat. Off.. |
| 4-187687 | 7/1992 | Japan. |
| WO 91/13070 | 9/1991 | WIPO. |
| WO 91/13071 | 9/1991 | WIPO. |
| WO 94/02488 | 2/1994 | WIPO. |
| WO 94/14798 | 3/1994 | WIPO. |
| WO 94/07895 | 4/1994 | WIPO. |

OTHER PUBLICATIONS

Godecke, "New indolo–pyrrolo–carbazole derivs,–useful as protein kinase inhibitors", Abstract 90–132947/18, Oct. 21, 1988.

Kaisha, "New indolocarbazole derivs. are proteinkinase C inhibitors—useful as anti–tumour agents, antihypertensives and macrophage activators," Abstract 92–274042/33, Nov. 20, 1990.

Alexakis, "Boron Trifluoride Assisted Opening of Epoxides by Lithium Alkenyl Aluminate Reagents," Tetrahedrom, 45:6197–6202 (1989).

Ansell, "The Synthesis of Some Olefinic Acids Using Tetrahydro–β–halogeno–furan and –pyran Derivatives as Intermediates," Chem. & Ind., pp. 1788–1795 (1956).

Behling, "The Synthesis of β–hydroxy–(E)–Vinylstannanes Using an In Situ Generated Cuprate Reagent Derived from (E)–Bis–(Tributylstannyl)Ethylene," Tetrahedron Letters, 30:27–30 (1989).

Bergman, "Coupling of Indoleaetic Acid Trianion or Methyl Indoleacetic Acid Dianion. A Biommetic Approach to Indolocarbazole Alkaloids," Tetrahedron Letters, 28:4441–4444 (1987).

Bit, "Inhibitors of Protein Kinase C. 3. Potent and Highly Selective Bisindolylmaleimides by Conformational Restriction," J. Med. Chem., 36:21–29 ((1993).

Bradshaw, "Therapeutic Potential of Protein Kinase C Inhibitors," Agents Actions, 38:135–147 (1993).

Brenner, "Synthesis of Arcyriarubin B and Related Bisindolymaleimides," Tetrahedron, 44:2887–2892 (1988).

Buchdunger, "4,5–Dianilinophthalimide: A Protein–tyrosine kinase inhibitor with Selectivity for the Epidermal Growth Factor Receptor Signal Transduction Pathway and Potent In Vivo Antitumor Acitivity," Proc. Natl. Acad. Sci., 91:2334–2338 (1994).

Davis, "A Mild Conversion of Maleic Anydrides into Maleimides," Tetrahedron Letters, 31:5201–5204 (1990).

Davis, "Inhibitors of Protein Kinase C. 2. Substituted Bisindolymaleimides with Improved Potency and Selectivity," J. Med. Chem., 35:994–1001 (1992).

Davis, "Inhibitors of Protein Kinase C. 1. 2,3–Bisarylmaleimides," J. Med. Chem., 35:177–184 (1992).

Demaerschalck, "Acitivation of Protein Kinase C Increases the Extracellular Release of the Transmembrane Amyloid Protein Precursor of Alzheimer's Disease," Biochemica et Biophysica Acta, 1181:214 (1993).

Edge, "An Improved Procedure for the Synthesis of N–substituted 3,4–Dichloromaleimides," Chem. & Ind., (1991).

Felsenstein, "Reversal of the Swedish Familial Alzheimer's Disease Mutant Phenotype in Cultured Cells Treated with Phorbol 12,13–Dibutyrate," Neuroscience Letters, 174:173–176 (1994).

(List continued on next page.)

Primary Examiner—Mukund J. Shah
Assistant Examiner—Pavanaram K. Sripada
Attorney, Agent, or Firm—Banner & Witcoff, Ltd.

[57] ABSTRACT

A method for treating endothelial cell dysfunction, such as associated with cardiovascular disease are disclosed, particularly using the isozyme selective PKC inhibitor, (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione hydrochloride salt.

50 Claims, No Drawings

OTHER PUBLICATIONS

Fieser, Reagents for Organic Synthesis, XII, John Wiley & Sons, p. 108 (1986).

Gillet, "Di- and Trifluorovinyllithium Reagents," Papers, pp. 355–360 (1986).

Harris, "Oxidative Cyclisations with Palladium Acetate. A Short Synthesis of Staurosporine Aglycone," Tetrahedron Letters, vol. 34;8361–8364 (1993).

Jirousek, "(S)–13–[(Dimethylamino)methyl]–10,11, 14, 15–tetrahydro–4.9:16,21–dimethenolH, 13H–dibenso[e,k] pyrrolo [3,4–h]oxadiazacyclohexadecene–1,3(2H)–dione (LY333531) and Related Analogues: Isozyme Selective Inhibitors of Protein Kinase Cβ," J. Med. Chem., pp. A–H (19960.

Joyce, "Synthesis of the Aromatic and Monosaccharide Moieties of Staurosporine," J. Org. Chem., 52:1177–1185 (1987).

Kaneko, "Two Synthetic Approaches to Rebeccamycin," Bristol–Myers Pharmaceutical R&D Division, Syracuse, N.Y, pp. 4015–4017.

Knaack, "Clonal Insulinoma Cell Line That Stably Maintains Correct Glucose Responsiveness," Diabetes, 1413–1417 (1994).

Kobayashi, "Platelet–activating factor modulates microvascular Transport by Stimulation of Protein Kinase C," The American Physiological Society, pp. H1214–H1220 (1994).

Krakowiak, "Improved Methods for the Synthesis of AZA––Crown Macrocycles and Cryptands,"Synlett, pp. 611–620 (1993).

Lipshutz, "Effects of Gengenions on Organoguprate Reactivity/Selectivity: Higher Order, Mixed Lithio–Sodio Cyanocuprates," Tetrahedron Letters, 29:893–896 (1988).

Martiny–Baron, "Selective Inhibition of Protein Kinase C Isozymnes by the Indolocarbazole Go 6976," J. Bio. Chem., 268:9194–9197 (1993).

Meier, "Preparation of Dithiacycloalkynes by Cyclization Reactions Applying the Cesium Effect," Tetrahedron Letters, 34:5277–5280 (19930.

Mulqueen, "Oral, Anti–Inflammatory Acitivity of a Potent, Selective, Protein Kinase C Inhibitor," Agents Actions, 37:85–89 (1992).

Nixon, "Novel, Potent and Selective Inhibitors of Protein Kinase C Show Oral Anti–Inflammatory Activity," Drugs Exptl. Clin. Res., XVII:389–393 (1991).

Rudloff, "Hydrogenolysis of Carbohydrates," Canadian J. Chem., ed. Leo Marion, 35:315–321 (1957).

Rosenthal, "The Reaction of Unsaturated Carbohydrates with Carbon Monoxide and Hydrogen. III. Structure and Stereochemistry of the Hexitols from 3,4–DI–O–Acetyl–d–Arabinal," Canadian J. Chem., 42:2025–2027 (1964).

Schuds, "A Short and Efficient Synthesis of 4,5–Disubstituted–1–Pentenes," Communications, pp. 309–312 (1985).

Shimohama, "Assessment of Protein Kinase C Isozymes by Two–Site Enzyme Immunoassay in Human Brains and Changes in Alzheimers' Disease," 43:1407–1413 (1993).

Steglich, "Indole Pigments from the Fruiting Bodies of the Slime Mold Arcyria denudata," Angew, Chem. Int. Ed. Engl. 19:459–460 (1980).

Tius, "Total Synthesis of (+)–Desepoxyasperdiol," J. Am. Chem. Soc., 108:1035–1039 (1985).

Toullec, "The Bisindolylmaleimide GF 109203X is a Potent and Selective Inhibitor of Protein Kinase C," J. Bio. Chem., 266:15771–15781 (1991).

Weinreb, "Natural Product Synthesis Via Cycloadditions with N–Sulfinyl Dienophiles," Heterocycles, 21:309–324 (1984).

Wilkinson, "Isoenzyme Specificity of Bisindolylmaleimides, Selective Inhibitors of Protein Kinase C," Biochem J., 294–335–337 (1993).

THERAPEUTIC TREATMENT FOR CARDIOVASCULAR DISEASES

This application is a continuation-in-part of Heath et al., application U.S. Ser. No. 08/643,706 filed May 6, 1996, pending which is a divisional of Heath et al., U.S. Ser. No. 08/413,735, filed Mar. 30, 1995 patented U.S. Pat. No. 5,624,949, which is a continuation-in-part of Heath et al., U.S. Ser. No. 08/316,973, filed Oct. 3, 1994 now abandoned, which is a continuation-in-part of Heath et al., U.S. Ser. No. 08/163,060, filed Dec. 7, 1993 now abandoned.

BACKGROUND OF THE INVENTION

1. The present invention is broadly directed to a method for treating vascular endothelial cell dysfunction, especially dysfunction induced by hyperglycemia. The present invention is particularly directed to the use of a particular class of isozyme selective Protein Kinase C (PKC) inhibitors for treating atherosclerotic disease states especially cardiovascular diseases associated with vascular endothelial cell dysfunction.

2. Description of Related Art

Injury or dysfunction of the vascular endothelium is a common feature shared by many conditions that predispose an individual to accelerated development of atherosclerotic cardiovascular disease. One of the most prevalent factors that causes endothelial cell dysfunction is hyperglycemia. Evidence suggests that hyperglycemia is directly toxic to endothelial cells. Using techniques such as acetylcholine induced vasodilation as an indicator of endothelial cell function, multiple studies have demonstrated that endothelial cell dysfunction is apparent in nonhuman models of diabetes. Several studies in humans have demonstrated that a similar dysfunction of the endothelium exists in humans with diabetes. Although certain types of diabetes are accompanied with other cardiovascular risk factors such as obesity, hypertension and dyslipidemias, these concomitant risk factors do not account for the increased risk of developing the clinical manifestations of atherosclerosis seen in diabetic patients.

Several groups have suggested that the occurrence of microalbuminuria in both diabetic and non-diabetic patients reflects a generalized worsening of their endothelial cell function. In diabetic patients, the onset of microalbuminuria is associated with a large increase in the risk of exhibiting the clinical manifestations of atherosclerotic macrovascular disease that is independent of other conventional cardiovascular risk factors. In non-diabetic populations, the onset of microalbuminuria is associated with an increase in the risk of developing macrovascular atherosclerosis and cardiovascular disease. Thus, the widespread endothelial cell dysfunction associated with the onset of microalbuminuria strongly correlates with a dramatic increase in cardiovascular disease. These findings suggest that vascular endothelial cell dysfunction may be the etiology explaining the increase in cardiovascular disease seen in both diabetic and non-diabetic patients with microalbuminuria. Furthermore, the treatment of microalbuminuria has been associated with a lowering of blood lipids and blood pressure.

In addition to predisposing a patient to chronic complications of atherosclerosis, vascular endothelial cell dysfunction also is associated with acute sequela of atherosclerosis such as ischemic-reperfusion injury. Both non-diabetic and diabetic patients are at increased risk of sudden death due mainly to cardiovascular causes. Diabetic patients also have an increased mortality rate following a myocardial infarction. The increased mortality rate after a myocardial infarction and the increased incidence of sudden death in diabetic patients can be related to a higher degree of vascular endothelial dysfunction imparted by hyperglycemia in addition to the intrinsic endothelial cell dysfunction associated with ischemia-reperfusion injury.

Populations without overt diabetes, but exhibiting milder elevations in their glucose levels, are also at an increased risk for the development of the clinical manifestations of atherosclerosis, e.g., cerebrovascular disease, peripheral vascular disease, myocardial ischemic states, and sudden death. Populations with impaired glucose tolerance have a higher prevalence of atherosclerotic diseases.

Data obtained in several diseases demonstrate that predispose to the development of atherosclerosis such as hypertension and hypercholesterolemia are associated with a dysfunctional endothelium and reversal of these factors that predispose the patient to atherosclerosis ameliorates the endothelial cell dysfunction. Correlating with the improvement in endothelial cell function, seen with reduction of hypercholesterolemia, is a reduction in cardiovascular events. Thus, treatments improving vascular endothelial cell function should reduce the risk of developing clinical manifestations of cardiovascular disease.

Protein kinase C activation occurs during ischemia-reperfusion in non-diabetic animal models and has been implicated in the pathogenesis of injury occurring in the ischemia-reperfusion model. In non-diabetic models of ischemia-reperfusion injury which simulates the pathologic processes occurring during acute myocardial ischemia, endothelial cell dysfunction occurs and is involved in worsening cardiac damage after this injury. Protection against endothelial cell damage in this model reduces myocardial injury after ischemia-reperfusion induced damage.

Given that the ischemia-reperfusion myocardial injury model is thought to reflect the processes occurring during acute myocardial ischemic states, such as myocardial infraction, treatment of non-diabetics patients suffering from acute myocardial ischemia with a PKC inhibitor are expected to exhibit a reduction in myocardial injury and the sequela related to this injury (e.g., arrhythmia, sudden death, increased infarction size, congestive heart failure, recurrent ischemia, etc.

The ubiquitous nature of the protein kinase C isozymes and their important roles in physiology provide incentives to produce highly selective PKC inhibitors. Given the evidence demonstrating linkage of certain isozymes to disease states, it is reasonable to assume that inhibitory compounds that are selective to one or two protein kinase C isozymes relative to the other PKC isozymes and other protein kinases are superior therapeutic agents. Such compounds should demonstrate greater efficacy and lower toxicity by virtue of their specificity.

At present, there are limited means to treat vascular endothelial cell dysfunction and the atherosclerotic disease states, especially cardiovascular diseases associated with it. Thus there is a need in the art to employ new therapeutic agents to treat atherosclerotic disease states especially cardiovascular diseases.

SUMMARY OF INVENTION

It is an object of the invention to provide a method for treating vascular endothelial cell dysfunction.

It is another object of the invention to provide a method for treating cardiovascular disease.

It is yet another object of the invention to provide a method for inhibiting onset of cardiovascular disease.

It is still another object of the invention to provide a method for treating microalbuminuria.

It is another object of the invention to provide a method for treating central ischemia brain injury.

It is yet another object of the invention to provide a method for treating restenosis.

It is still another object of the invention to provide a method for treating atherosclerosis.

These and other objects of the invention are provided by one or more of the embodiments described below.

In one embodiment of the invention there is provided a method for treating vascular endothelial cell dysfunction which comprises contacting said vascular endothelial cells with a cell dysfunction inhibiting amount of a particular protein kinase C inhibitor.

In another embodiment of the invention there is provided a method for treating cardiovascular disease which comprises administering to a mammal in need of such treatment, a therapeutically effective amount of a particular protein kinase C inhibitor.

In still another embodiment of the invention there is provided a method for inhibiting onset of cardiovascular disease in a mammal, which comprises administering to the mammal in need of such treatment, a therapeutically effective amount of a particular protein kinase C inhibitor.

In another embodiment of the invention there is provided a method for treating microalbuminuria which comprises administering to a mammal in need of such treatment, a therapeutically effective amount of a particular protein kinase C inhibitor.

In still another embodiment of the invention there is provided a method for treating central ischemia brain injury which comprises administering to a mammal in need of such treatment, a therapeutically effective amount of a particular protein kinase C inhibitor.

In yet another embodiment of the invention there is provided a method for treating restenosis which comprises administering to a mammal in need of such treatment, a therapeutically effective amount of a particular protein kinase C inhibitor.

In still another embodiment of the invention there is provided a method for treating atherosclerosis which comprises administering to a mammal in need of such treatment, a therapeutically effective amount of a particular protein kinase C inhibitor.

The present invention provides the art with compounds which are prophylactic and effective in treating vascular endothelial cell dysfunction. Consequently, the compounds can be used to treat or inhibit the onset of atherosclerotic disease states, especially cardiovascular diseases associated with vascular endothelial cell dysfunction.

DETAILED DESCRIPTION OF THE INVENTION

It is a discovery of the present invention that using a particular class of protein kinase C inhibitors reduces vascular endothelial cell dysfunction associated with atherosclerotic disease states, and in particular the endothelial cell dysfunction induced by hyperglycemia. Consequently, such compounds can be used therapeutically to treat a variety of atherosclerotic disease states especially cardiovascular diseases, and prophylactically to inhibit the development of such diseases.

The method of this invention preferably utilizes the isozyme selective protein kinase C inhibitor compounds of formula I:

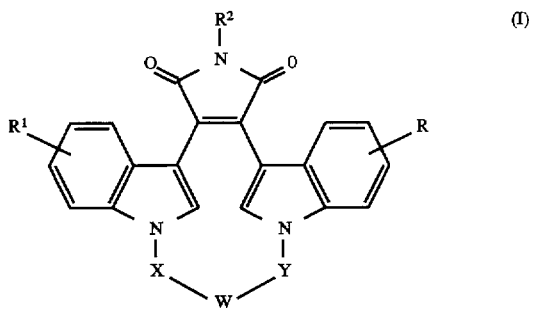

wherein:

W is —O—, —S—, —SO—, —SO$_2$—, —CO—, C$_2$-C$_6$ alkylene, substituted alkylene, C$_2$-C$_6$ alkenylene, -aryl-, -aryl(CH$_2$)$_m$O—, -heterocycle-, -heterocycle-(CH$_2$)$_{2m}$O—, -fused bicyclic-, -fused bicyclic-(CH$_2$)$_m$O—, —NR$^3$—, —NOR$^3$—, —CONH—, or —NHCO—;

X and Y are independently C$_1$-C$_4$ alkylene, substituted alkylene, or together X, Y, and W combine to form —(CH$_2$)$_n$—AA—;

R$^1$s are hydrogen or up to four optional substituents independently selected from halo, C$_1$-C$_4$ alkyl, hydroxy, C$_1$-C$_4$ alkoxy, haloalkyl, nitro, NR$^4$R$^5$, or —NHCO(C$_1$-C$_4$ alkyl);

R$^2$ is hydrogen, CH$_3$CO—, NH$_2$, or hydroxy;

AA is an amino acid residue.

These compounds, and methods for their preparation, are known and have been disclosed in Heath et al., EP publication 0 657 458 A1 which is incorporated herein by reference. These compounds are administered in a therapeutically effective amount, e.g., a vascular endothelial cell dysfunction inhibiting amount, to a mammal to treat endothelial cell dysfunction. The endothelial cell dysfunction can be induced by a variety of factors, e.g., hyperglycemia, hypertension, hypercholesterolemia, and ischemic-reperfusion injury.

Such endothelial cell dysfunction can be associated with atherosclerotic disease states including cerebrovascular diseases, e.g., central ischemia brain injury, cerebrovascular accidents and transient ischemic attacks; peripheral vascular diseases, e.g., nontraumatic amputations and intermittent claudication, and cardiovascular diseases, e.g., stable angina, unstable angina, variant angina, sudden death, myocardial infarction, restenosis, and ischemia-reperfusion injury. Consequently, these compounds can be used to treat these various atherosclerotic disease states, especially the cardiovascular diseases discussed above.

The compounds also can be administered in a prophylactically effective amount to patients at risk of developing atherosclerotic disease states, especially cardiovascular diseases, such as patients with hyperglycemia, hypertension, or hypercholesterolemia, as a prophylactic.

The preferred compounds for use in this invention are those of formula I wherein the moieties —X—W—Y— contain 4 to 8 atoms, which may be substituted or unsubstituted. Most preferably, the moieties —X—W—Y— contain 6 atoms.

Other preferred compounds for use in this invention are those compounds of formula I wherein R$^1$ and R$^2$ are hydrogen; and W is a substituted alkylene, —O—, S—, —CONH—, —NHCO— or —NR³—. Particularly preferred compounds are compounds of the formula Ia:

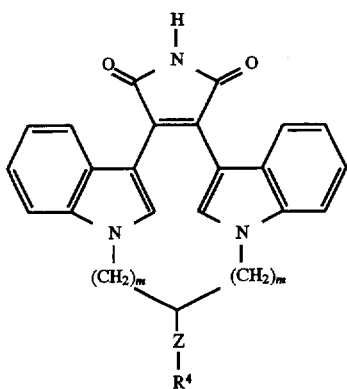

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_p$aryl, —NH(aryl), —N(CH$_3$)(CF$_3$), —NH(CF$_3$), or —NR$^{R6}$; R$^5$ is hydrogen or C$_1$–C$_4$ alky; R$^6$ is hydrogen, C$_1$–C$_4$ alkyl or benzyl; p is 0, 1, or 2; and m is independently 2 or 3. Most preferred compounds of the formula Ia are those wherein Z is —CH$_2$; and R$^4$ is —NH$_2$, —NH(CF$_3$), or —N(CH$_3$)$_2$.

Other preferred compounds for use in the present invention are compounds wherein W in formula I is —O—, Y is a substituted alkylene, and X is an alkylene. These preferred compounds are represented by formula Ib:

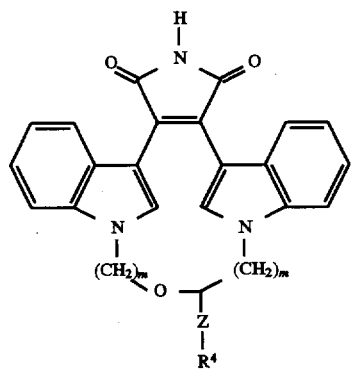

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3. Most preferred compounds of formula Ib are those wherein p is 1; and R$^5$ and R$^6$ are methyl.

Because they contain a basic moiety, the compounds of formula I, Ia and Ib can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and the like.

In addition to pharmaceutically-acceptable salts, other salts also can exist. They may serve as intermediates in the purification of the compounds, in the preparation of other salts, or in the identification and characterization of the compounds or intermediates.

The pharmaceutically acceptable salts of compounds of formulae I, Ia and Ib can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of formulae I, Ia and Ib may exist; for example, W may contain a chiral carbon atom in the substituted alkylene moiety. The compounds are normally prepared as racemates and can conveniently be used as such. Alternatively, both individual enantiomers can be isolated or synthesized by conventional techniques if so desired. Such racemates and individual enantiomers and mixtures thereof form part of the compounds used in the methods of the present invention.

The compounds utilized in this invention also encompass the pharmaceutically acceptable prodrugs of the compounds of formulae I, Ia and Ib. A prodrug is a drug which has been chemically modified and may be biologically inactive at its site of action, but which may be degraded or modified by one or more enzymatic or other in vivo processes to the parent bioactive form. This prodrug likely may have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H. Bundgaard, *Design of Prodrugs*, (1985).

The synthesis of various bis-indole-N-maleimide derivatives is described in Davis et al. U.S. Pat. No. 5,057,614 and the synthesis of the preferred compounds suitable for use in this invention are described in the previously identified Heath et al.0 EP publication 657 458 and in Faul et al. EP publication 0 657 411 A1, both of which are incorporated herein by reference.

One particularly preferred protein kinase C inhibitor for use in the method of this invention is the compound described in Example 5s ((S)-3,4-[N,N'-1,1'-((2"-ethoxy)-3'"(O)-4'"(N,N-dimethylamino)-butane)-bis-(3,3'-indolyl)]-1(H)-pyrrole-2,5-dione Hydrochloride Salt) of the aforementioned EP publication 0 657 458 A1. This compound is a potent protein kinase C inhibitor. It is selective to protein kinase C over other kinases and is highly isozyme-selective, i.e., it is selective for the beta-1 and beta -2 isozymes. This compound is shown to normalize endothelial cell dysfunction in animal models of diabetes at doses predictive to selectively inhibit PKC-β. The data are reported in Hidehiro et al., *Science* Vol. 272, page 728–731, 1996 and is incorporated herein by reference.

In streptozotocin and alloxan diabetic rodents, this compound normalized changes induced by diabetes in retinal blood flow and vascular Na/K-ATPase activity. Changes in retinal blood flow reflect hyperglycemic induced abnormalities in endothelial cell regulation of blood flow. Decreases in Na/K-ATPase activity is a indication of abnormal endothelial cell function (Gupta, et al., *J. Clin. Invest.*, 90:727–732 (1991)). The ability of this compound to normalize these diabetic induced abnormalities demonstrates its protective effect on the endothelium in hyperglycemic states. In addition, this compound blocked microalbuminuria, a marker of widespread endothelial cell dysfunction. Thus, in the rodent model of diabetes, this compound reduces the glucose-mediated endothelial cell toxicity and inhibited the endothelial cell dysfunction that is associated with the development of atherosclerotic macrovascular disease.

Vascular endothelial cell dysfunction is strongly associated with atherosclerotic cardiovascular disease in diabetic and nondiabetic patients. The compounds of this invention, being active for normalizing vascular endothelia cell dysfunctions are particularly useful for treating cardiovascular diseases e.g., stable angina, unstable angina, variant angina, cardiovascular ischemia, sudden death, and myocardial infarction, especially the cardiovascular diseases associated with hyperglycemia. In addition to predisposing individuals to chronic complications of atherosclerosis, endothelial cell dysfunction also is associated with acute sequela of atherosclerosis such as ischemic-reperfusion injury (Ku, *Science*, 218:576–578 (1982); Van Benthuysen, et al., *J. Clin. Invest.*, 79:265–274 (1987); Mehta, et al., *Cir. Res.*, 64:43–54 (1989)). The compounds useful in the method of this invention are therapeutically effective for reducing endothelial cell dysfunction occurring after an ischemic episode and on reducing the clinical sequela associated with this abnormality, e.g., sudden death and a higher mortality rate after a myocardial infarction.

The compounds of this invention also can be used to reduce the risk of cardiovascular disease seen in persons exhibiting hyperglycemia. A normal range of plasma glucose level is 75 to 105 mg/dl (4.2 to 5.8 mmol per liter) in fasting condition and up to 140 mg/dl (up to 7.8 mmol per liter) two hours postprandial. The compounds thus can be used prophylactively to treat patients where glucose levels are in the upper range of normal and in patients exhibiting impaired glucose tolerance, hypertension, hypercholesterolemia, and diabetes.

Microalbuminuria and macrovascular endothelial cell dysfunction reflect a generalized worsening of vascular endothelial cell function in diabetic and non-diabetic patients. The compounds in the present invention can be used, therapeutically to treat these conditions.

The term "treating," as used herein, describes the management and care of a patient for the purpose of combating the disease, condition, or disorder and includes the administration of a compound of present invention to prevent the onset of the symptoms or complications (prophylactic uses), alleviating the symptoms or complications, or eliminating the disease, condition, or disorder.

The term "isozyme selective" means the preferential inhibition of protein kinase C beta-1 or beta-2 isozyme over protein kinase C isozymes, alpha, gamma, delta, epsilon, zeta, and eta. In general, the compounds useful in the invention demonstrate a minimum of a eight fold differential (preferably a ten fold differential) in the dosage required to inhibit PKC beta-1 or beta-2 isozyme and the dosage required for equal inhibition of the alpha protein kinase C isozyme as measured in the PKC assay. The compounds demonstrate this differential across the range of inhibition and are exemplified at the $IC_{50}$, i.e., a 50% inhibition. Thus, isozyme-selective compounds inhibit the beta-1 and beta-2 isozymes of protein kinase C at much lower concentrations with lower toxicity by virtue of their minimal inhibition of the other PKC isozymes.

One skilled in the art will recognize that a therapeutically effective amount, e.g., an endothelial cell dysfunction inhibiting amount, of the protein kinase C inhibitor of the present invention is an amount sufficient to inhibit the endothelial cell dysfunction or inhibit development of cardiovascular disease and that this amount varies inter alia, depending upon an affected tissue size, the concentration of the compound in the therapeutic formulation, and the body weight of the patient. Generally, an amount of protein kinase C inhibitor to be administered as a therapeutic agent for treating cardiovascular disease, and for inhibiting onset of cardiovascular disease as discussed above, will be determined on a case by case basis by the attending physician. As a guideline, the extent of the vascular endothelial cell dysfunctions, the body weight, and age of the patient will be considered when setting an appropriate dose.

Generally, a suitable dose is one that results in a concentration of the protein kinase C inhibitor at the treatment site in the range of 0.5 nM to 200 µM, and more usually 0.5 nM to 200 nM. It is expected that serum concentrations of 0.5 nM to 10 nM should be sufficient in most circumstances.

To obtain these treatment concentrations, a patient in need of treatment likely will be administered between about 0.001 mg per day per kg of body weight and 50.0 mg per day per kg. Usually, not more than about 10.0 mg per day per kg of body weight of protein kinase C inhibitor need be needed. As noted above, the above amounts may vary on a case-by-case basis.

One skilled in the art will also recognize that a prophylactically effective amount of the protein kinase C inhibitor of the present invention is an amount sufficient to inhibit or reduce the risk of onset of cardiovascular disease. This amount varies depending on the degrees of exhibited risk factors. Generally, an amount of protein kinase C inhibitor to be administered as a prophylactic agent for cardiovascular disease will be determined on a case by case basis by the attending physicians. As a guideline, a suitable dose is determined on the dose of the PKC inhibitors used as therapeutic agents. It normally would range from 50% –150% of the therapeutic dosage discussed above.

The compounds of formula I, and the preferred compounds of formulae Ia and Ib, are preferably formulated prior to administration. Suitable pharmaceutical formulations are prepared by known procedures using well known and readily available ingredients. In making the compositions suitable for use in the method of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application.

Some examples of suitable carriers, excipient, and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents.

The compositions of the invention may be formulated so as to provide quick, sustained or delayed release of the active ingredient after administration to the patient. The compositions are preferably formulated in a unit dosage form, each dosage containing from about 0.05 mg to about 3 g, more usually about 750 mg of the active ingredient. However, it will be understood that the therapeutic dosage administered will be determined by the physician in the light of the relevant circumstances, including the severity of the condition to be treated, the choice of compound to be administered and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, most of which may be administered orally, the compounds used in the method of the present invention also may be administered topically. Topical formulations include ointments, creams and gels.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of PKC inhibitor compound incorporated into a topical formulation is not critical; the concentration should be within a range sufficient to permit ready application of the formulation to the affected tissue area in an amount which will deliver the desired amount of compound to the desired treatment site.

The customary amount of a topical formulation to be applied to an affected tissue will depend upon an affected tissue size and concentration of compound in the formulation. Generally, the formulation will be applied to the effected tissue in an amount affording from about 1 to about 500 µg compound per $cm^2$ of an affected tissue. Preferably, the applied amount of compound will range from about 30 to about 300 µg/$cm^2$, more preferably, from about 50 to about 200 µg/$cm^2$, and, most preferably, from about 60 to about 100 µg/$cm^2$.

The following formulation examples are illustrative only and are not intended to limit the scope of the invention in any way.

FORMULATION 1

Hard gelatin capsules are prepared using the following ingredients:

| | Quantity (mg/capsule) |
|---|---|
| Active agent | 250 |
| starch, dried | 200 |
| magnesium stearate | 10 |
| Total | 460 mg |

The above ingredients are mixed and filled into hard gelatin capsules in 460 mg quantities.

FORMULATION 2

A tablet is prepared using the ingredients below:

| | Quantity (mg/capsule) |
|---|---|
| Active agent | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

FORMULATION 3

Tablets each containing 60 mg of active ingredient are made as follows:

| | Quantity (mg/tablet) |
|---|---|
| Active agent | 60 mg |
| starch | 45 mg |
| microcyrstalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 4

Capsules each containing 80 mg of medicament are made as follows:

| | Quantity (mg/capsule) |
|---|---|
| Active agent | 80 mg |
| starch | 59 mg |
| microcrystalline cellulose | 59 mg |
| magnesium stearate | 2 mg |
| Total | 220 mg |

The active ingredient, cellulose, starch and magnesium stearate are blended, passed through a No. 45 mesh U.S. sieve, and filled into hard gelatin capsules in 200 mg quantities.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A method for treating vascular endothelial cell dysfunction in a mammal comprising administering to a mammal in need of such treatment a cell dysfunction inhibiting amount of a protein kinase C inhibitor, wherein the protein kinase C inhibitor has the following formula:

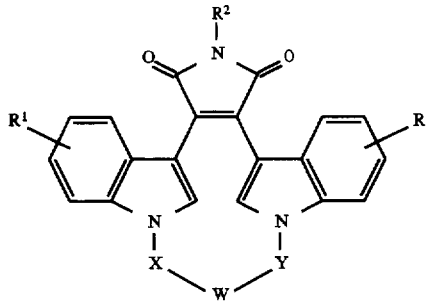

wherein:

W is —O—, —S—, —SO—, —SO$_2$—, —CO—, C$_2$-C$_6$ alkylene, substituted alkylene, C$_2$-C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$-C$_4$ alkylene, substituted alkylene, or together X, Y, and W combine to form —(CH$_2$)$_n$—AA—;

R$^1$s are hydrogen or up to four optional substituents independently selected from halo, C$_1$-C$_4$ alkyl, hydroxy, C$_1$-C$_4$ alkoxy, haloalkyl, nitro, NR$^4$R$^5$, or —NHCO(C$_1$-C$_4$ alkyl);

R$^2$ is hydrogen, CH$_3$CO—, NH$_2$, or hydroxy; and

AA is an amino acid residue.

2. The method of claim 1 wherein the protein kinase C inhibitor has the following formula:

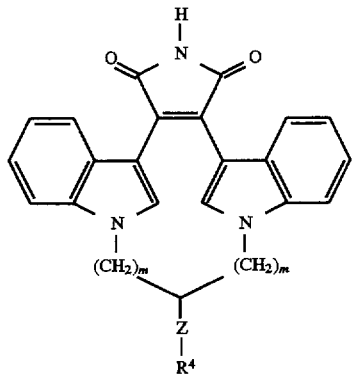

wherein Z is —(CH$_2$)$_p$— or —(CH$_2$)$_p$—O—(CH$_2$)$_p$—; R$^4$ is hydroxy, —SH, C$_1$-C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$-C$_4$ alky; R$^6$ is hydrogen, C$_1$-C$_4$ alkyl or benzyl; p is 0, 1, or 2; and m is independently 2 or 3.

3. The method of claim 1 wherein the protein kinase C inhibitor has the following formula:

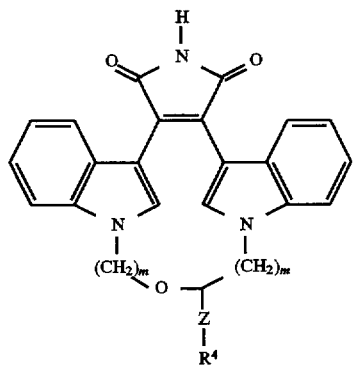

wherein Z is —(CH$_2$)$_p$—; R$^4$ is —NR$^5$R$^6$, —NH(CF$_3$), or —N(CH$_3$) CF$_3$); R$^5$ and R$^6$ are independently H or C$_1$-C$_4$ alkyl; p is 0, 1, or 2; and m is independently 2 or 3.

4. The method of claim 1, wherein the protein kinase C inhibitor comprises (S)-3,4-[N,N'-1,1'-((2"-ethoxy)-3'"(O)-4'"(N,N-dimethylamino)-butane)-bis-(3,3'-indolyl)]-1(H)-pyrrole-2,5-dione or its acid salt.

5. The method of claim 1 wherein the endothelial cell dysfunction is associated with hyperglycemia.

6. The method of claim 1 wherein the endothelial cell dysfunction is associated with ischemic-reperfusion injury.

7. A method for treating cardiovascular disease, which comprises administering to a mammal in need of such treatment, a therapeutically effective amount of a protein kinase C inhibitor, wherein the protein kinase C inhibitor has the following formula:

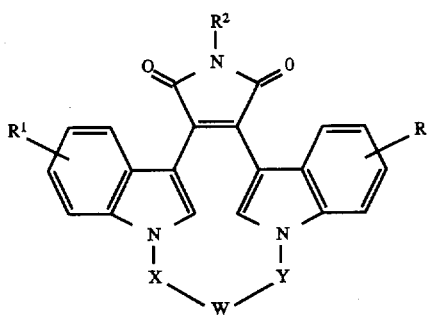

wherein:

W is —O—, —S—, —SO—, —SO$_2$—, —CO—, C$_2$-C$_6$ alkylene, substituted alkylene, C$_2$-C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$-C$_4$ alkylene, substituted alkylene, or together X, Y, and W combine to form —(CH$_2$)$_n$—AA—;

R$^1$s are hydrogen or up to four optional substituents independently selected from halo, C$_1$-C$_4$ alkyl, hydroxy, C$_1$-C$_4$ alkoxy, haloalkyl, nitro, NR$^4$R$^5$, or —NHCO(C$_1$-C$_4$ alkyl);

R$^2$ is hydrogen, CH$_3$CO—, NH$_2$, or hydroxy; and

AA is an amino acid residue.

8. The method of claim 7 wherein the protein kinase C inhibitor has the following formula:

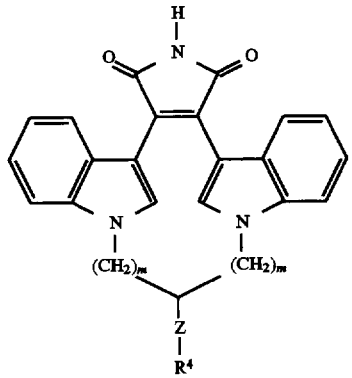

wherein Z is —(CH$_2$)$_p$— or —(CH$_2$)$_p$—O—(CH$_2$)$_p$—; R$^4$ is hydroxy, —SH, C$_1$-C$_4$ alkyl, (CH$_2$)$_m$aryl, —NH(aryl), —N(CH$_3$)(CF$_3$), —NH(CF$_3$), or —NR$^3$R$^6$; R$^5$ is hydrogen or C$_1$-C$_4$ alky; R$^6$ is hydrogen, C$_1$-C$_4$ alkyl or benzyl; p is 0, 1, or 2; and m is independently 2 or 3.

9. The method of claim 7 wherein the protein kinase C inhibitor has the following formula:

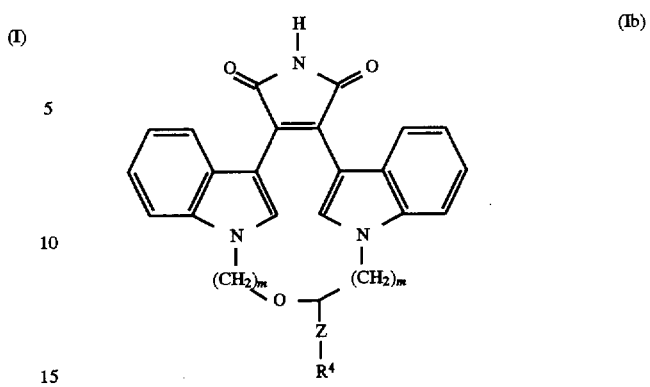

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$-C$_4$ alkyl; p is 0, 1, or 2; and m is independently 2 or 3.

10. The method of claim 7, wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or its acid salt.

11. The method of claim 7, wherein the cardiovascular disease is selected from a group consisting of stable angina, unstable angina, variant angina, cardiovascular ischemia, ischemia-reperfusion injury, sudden death, and myocardial infarction.

12. The method of claim 7, wherein the cardiovascular disease is associated with hyperglycemia.

13. A method for inhibiting onset of cardiovascular disease in a mammal, which comprises administering to a mammal a prophylactically effective amount of a protein kinase C inhibitor, wherein the protein kinase C inhibitor has the following formula:

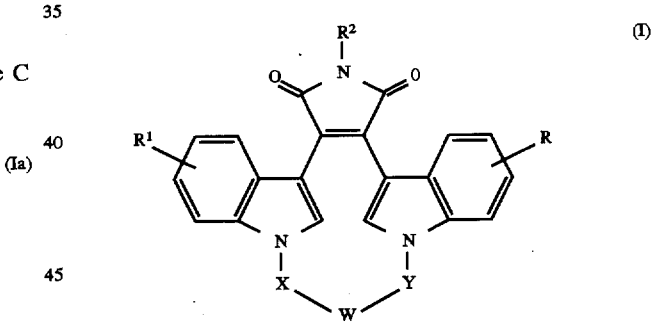

wherein:

W is —O—, —S—, —SO—, —SO$_2$—, —CO—, C$_2$-C$_6$ alkylene, substituted alkylene, C$_2$-C$_6$ alkenylene, -aryl-, -aryl(CH$_2$)$_m$O—, -heterocycle-, -heterocycle-(CH)Q—$_m$-fused bicyclic-, -fused bicyclic-(CH$_2$)$_m$O—, —NR$^3$—, —NOR$^3$—, —CONH—, or —NHCO—;

X and Y are independently C$_1$-C$_4$ alkylene, substituted alkylene, or together X, Y, and W combine to form —(CH$_2$)$_n$—AA—;

R$^1$s are hydrogen or up to four optional substituents independently selected from halo, C$_1$-C$_4$ alkyl, hydroxy, C$_4$-C$_4$ alkoxy, haloalkyl, nitro, NR$^4$R$^5$, or —NHCO(C$_1$-C$_4$ alkyl);

R$^2$ is hydrogen, CH$_3$CO—, NH$_2$, or hydroxy; and

AA is an amino acid residue.

14. The method of claim 13 wherein the protein kinase C inhibitor has the following formula:

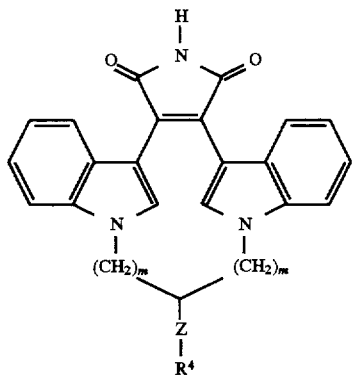

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alky; R$^6$ is hydrogen, C$_1$–C$_4$ alkyl or benzyl; p is 0, 1, or 2; and m is independently 2 or 3.

15. The method of claim 13 wherein the protein kinase C inhibitor has the following formula:

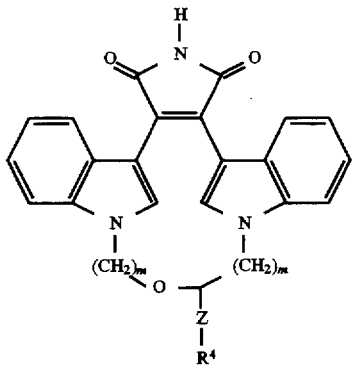

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3.

16. The method of claim 13, wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or it acid salt.

17. A method for treating microalbuminuria, which comprises administering to a mammal in need of such treatment, a therapeutically effective amount of a protein kinase C inhibitor, wherein the protein kinase C inhibitor has the following formula:

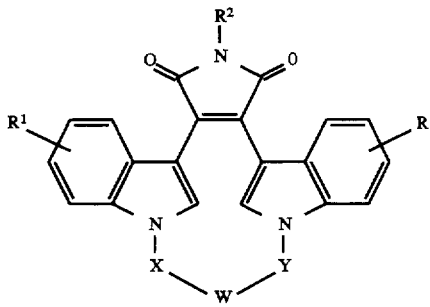

(I)

wherein:

W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_m$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy; and

AA is an amino acid residue.

18. The method of claim 17 wherein the protein kinase C inhibitor has the following formula:

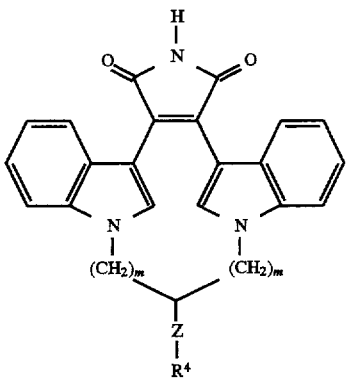

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alky; R$^6$ is hydrogen, C$_1$–C$_4$ alkyl or benzyl; p is 0, 1, or 2; and m is independently 2 or 3.

19. The method of claim 17 wherein the protein kinase C inhibitor has the following formula:

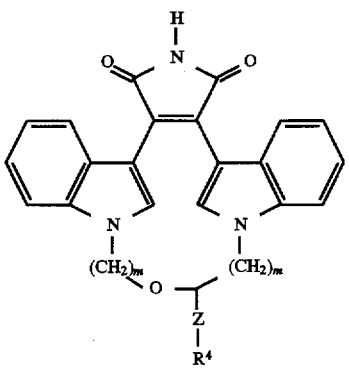

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3.

20. The method of claim 17, wherein the protein kinase C inhibitor comprises (S)-3,4-[N,N'-1,1'-((2"-ethoxy)-3'"(O)-4'"(N,N-dimethylamino)-butane)-bis-(3,3'-indolyl)]-1(H)-pyrrole-2,5-dione or its acid salt.

21. The method of claim 17, wherein microalbuminuria is associated with diabetes.

22. A method for treating central ischemia brain injury, which comprises administering to a mammal in need of such treatment, a therapeutically effective amount of a protein kinase C inhibitor, wherein the protein kinase C inhibitor has the following formula:

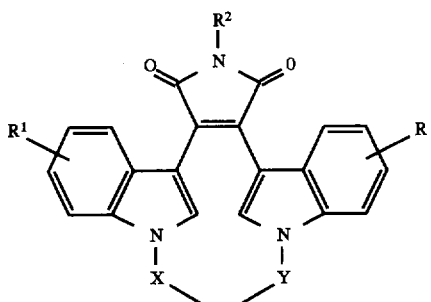

(I)

wherein:

W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy; and

AA is an amino acid residue.

23. The method of claim 22 wherein the protein kinase C inhibitor has the following formula:

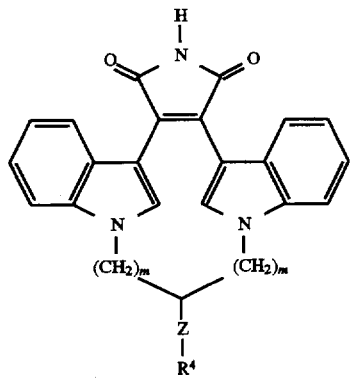

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alky; R$^6$ is hydrogen, C$_1$–C$_4$ alkyl or benzyl; p is 0, 1, or 2; and m is independently 2 or 3.

24. The method of claim 22 wherein the protein kinase C inhibitor has the following formula:

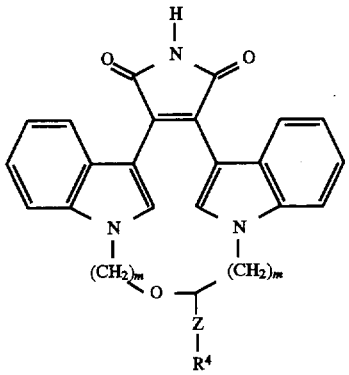

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3.

25. The method of claim 22, wherein the protein kinase C inhibitor comprises (S)-3,4-[N,N'-1,1'-((2''-ethoxy)-3'''(O)-4'''-(N,N-dimethylamino)-butane)-bis-(3,3'-indolyl)]-1(H)-pyrrole-2,5-dione or its acid salt.

26. A method for treating restenosis, which comprises administering to a mammal in need of such treatment, a therapeutically effective amount of a protein kinase C inhibitor, wherein the protein kinase C inhibitor has the following formula:

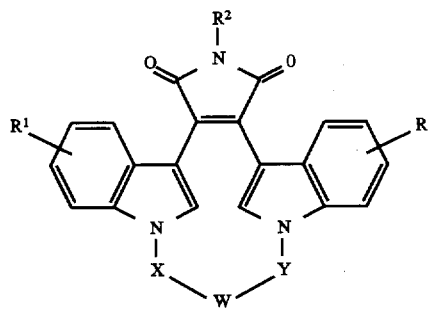

(I)

wherein:

W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy; and

AA is an amino acid residue.

27. The method of claim 26 wherein the protein kinase C inhibitor has the following formula:

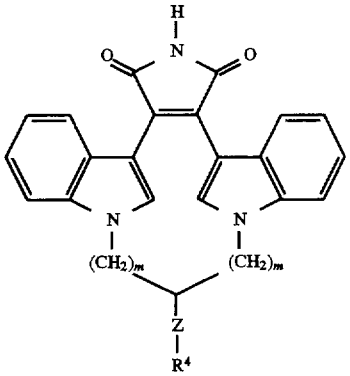

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alky; R$^6$ is hydrogen, C$_1$–C$_4$ alkyl or benzyl; p is 0, 1, or 2; and m is independently 2 or 3.

28. The method of claim 26 wherein the protein kinase C inhibitor has the following formula:

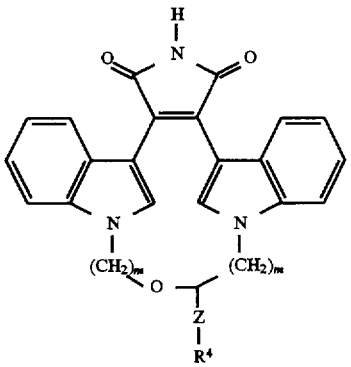

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3.

29. The method of claim 26, wherein the protein kinase C inhibitor comprises (S)-3,4-[N,N'-1,1'-((2"-ethoxy)-3'"(O)-4'"(N,N-dimethylamino)-butane)-bis-(3,3'-indolyl)]-1(H)-pyrrole-2,5-dione or its acid salt.

30. A method for treating atherosclerotic disease state, which comprises administering to a mammal in need of such treatment, a therapeutically effective amount of a protein kinase C inhibitor, wherein the protein kinase C inhibitor has the following formula:

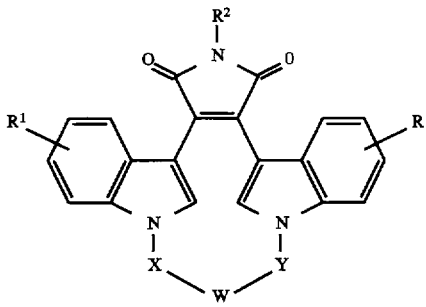

(I)

wherein:

W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy; and

AA is an amino acid residue.

31. The method of claim 30 wherein the protein kinase C inhibitor has the following formula:

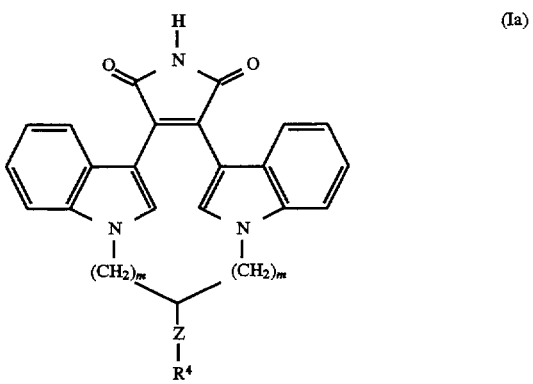

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alky; R$^6$ is hydrogen, C$_1$–C$_4$ alkyl or benzyl; p is 0, 1, or 2; and m is independently 2 or 3.

32. The method of claim 30 wherein the protein kinase C inhibitor has the following formula:

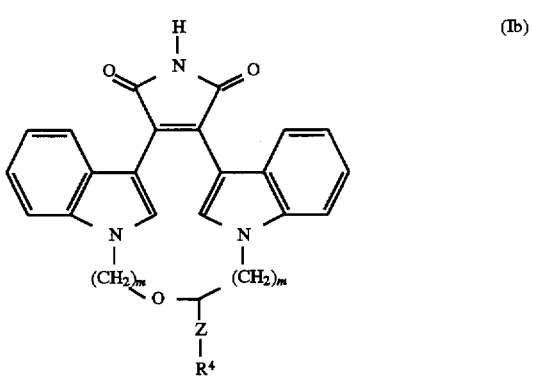

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3.

33. The method of claim 30, wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or its acid salt.

34. The method of claim 30, wherein the atherosclerotic disease state is selected from a group consisting of: cerebrovascular disease, peripheral vascular disease, and cardiovascular disease.

35. A method for treating congestive heart failure in a mammal comprising administering to a mammal in need of such treatment a therapeutically effective amount of a protein kinase C inhibitor, wherein the protein kinase C inhibitor has the following formula:

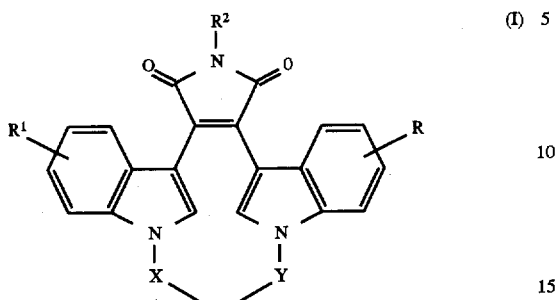

(I)

wherein:

W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy; and

AA is an amino acid residue.

36. The method of claim 35 wherein the protein kinase C inhibitor has the following formula:

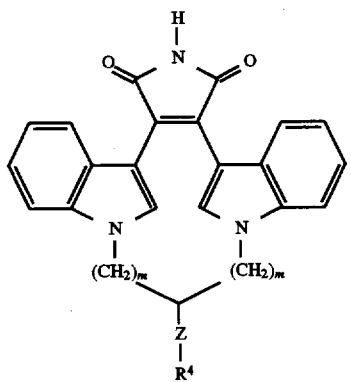

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alky; R$^6$ is hydrogen, C$_1$–C$_4$ alkyl or benzyl; p is 0, 1, or 2; and m is independently 2 or 3.

37. The method of claim 35 wherein the protein kinase C inhibitor has the following formula:

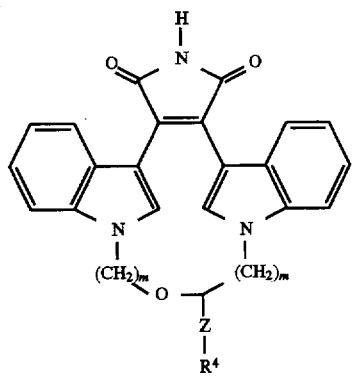

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3.

38. The method of claim 35, wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or its acid salt.

39. A method for treating congestive heart failure associated with vascular endothelial cell dysfunction in a mammal comprising administering to a mammal in need of such treatment a therapeutically effective amount of a protein kinase C inhibitor, wherein the protein kinase C inhibitor has the following formula:

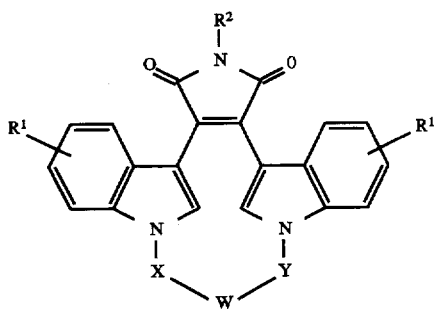

(I)

wherein:

W is —O—, —S—, —SO—, —SO$_2$—, —CO—, C$_2$–C$_6$alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_{1-4}$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy; and

AA is an amino acid residue.

40. The method of claim 39 where the protein kinase C inhibitor has the following formula:

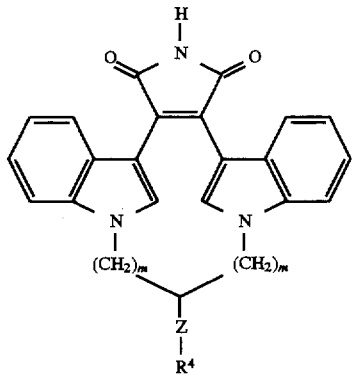

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alky; R$^6$ is hydrogen, C$_1$–C$_4$ alkyl or benzyl; p is 0, 1, or 2; and m is independently 2 or 3.

41. The method of claim 39 wherein the protein kinase C inhibitor has the following formula:

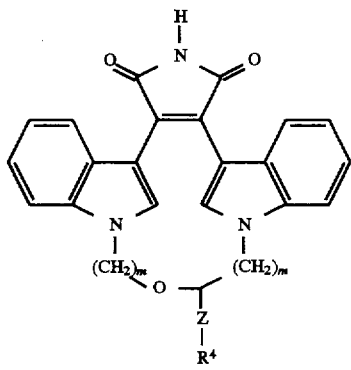

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3.

42. The method of claim 39, wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1-(H)-pyrrole-2,5-dione or its acid salt.

43. A method for treating congestive heart failure associated with myocardial injury in a mammal comprising administering to a mammal in need of such treatment a therapeutically effective amount of a protein kinase C inhibitor, wherein the protein kinase C inhibitor has the following formula:

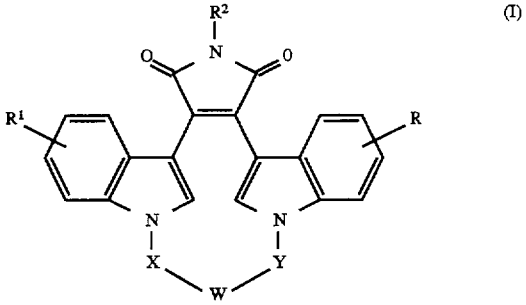

wherein:

W is —O—, —S—, —SO—, —SO$_2$—, —CO—, C$_2$–C$_6$ alkylene, substituted alkenylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$, —CONH—, or —NHCO—;

X and Y are independently C$_1$–C$_1$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_1$–alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy; and

AA is an amino acid residue.

44. The method of claim 43 wherein the protein kinase C inhibitor has the following formula:

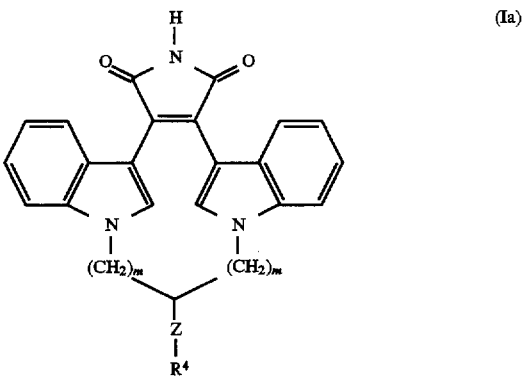

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alky; R$^6$ is hydrogen, C$_1$–C$_4$ alkyl or benzyl; p is 0, 1, or 2; and m is independently 2 or 3.

45. The method of claim 43 wherein the protein kinase C inhibitor has the following formula:

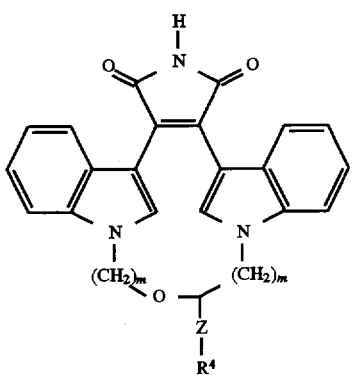

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3.

46. The method of claim 43, wherein the protein kinase C inhibitor comprises (S)-3,4-[N,N'-1,1'-((2"-ethoxy)-3'"(O)-4'"-(N,N-dimethylamino)-butane)-bis-(3,3-indolyl)]-1(H)-pyrrole-2,5-dione or its acid salt.

47. A method for treating congestive heart failure associated with atherosclerosis in a mammal comprising administering to a mammal in need of such treatment a therapeutically effective amount of a protein kinase C inhibitor, wherein the protein kinase C inhibitor has the following formula:

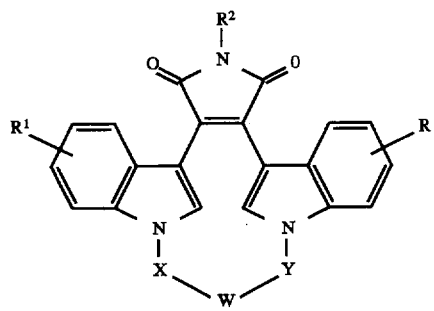

wherein:

W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy; and

AA is an amino acid residue.

48. The method of claim 47 wherein the protein kinase C inhibitor has the following formula:

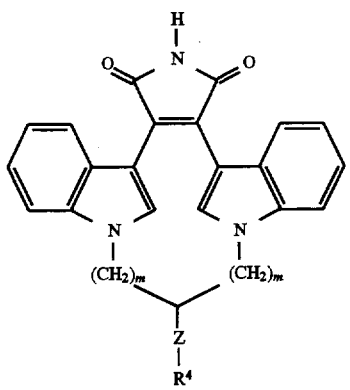

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alky; R$^6$ is hydrogen, C$_1$–C$_4$ alkyl or benzyl; p is 0, 1, or 2; and m is independently 2 or 3.

49. The method of claim 47 wherein the protein kinase C inhibitor has the following formula:

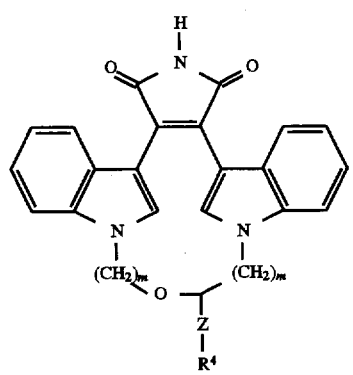

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3.

50. The method of claim 47, wherein the protein kinase C inhibitor comprises (S)-3,4-[N,N'-1,1'-(2"-ethoxy)-3'"(O)-4'"-(N,N-dimethylamino)-butane)-bis-(3,3'-indolyl)]-1(H)-pyrrole-2,5-dione or its acid salt.

* * * * *

UNITED STATES PATENT AND TRADEMARK OFFICE
CERTIFICATE OF CORRRECTION

PATENT NO. : 5,723,456
DATED : March 3, 1998
INVENTOR(S) : Michael R. Jirousek, et al.

It is certified that error appears in the above-identified patent and that said Letters Patent is hereby corrected as shown below:

Title page,
Item [56] Referecences Cited, please add the following patents and publications:

U. S. PATENT DOCUMENTS

| EXAMINER INITIAL | | PATENT NUMBER | | | | | | | ISSUE DATE | PATENTEE | CLASS | SUBCLASS | FILING DATE IF APPROPRIATE |
|---|---|---|---|---|---|---|---|---|---|---|---|---|---|
| | | 5 | 5 | 5 | 9 | 2 | 2 | 8 | 09/24/96 | Gillig | 540 | 460 | |
| | | 5 | 6 | 2 | 1 | 0 | 9 | 8 | 04/15/97 | Heath | 540 | 472 | |

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | | | | | | | | | | | | |

UNITED STATES PATENT AND TRADEMARK OFFICE
CERTIFICATE OF CORRECTION

PATENT NO. : 5,723,456
DATED : March 3, 1998
INVENTOR(S) : Michael R. Jirousek, William Francis Heath, Jr., Douglas Kirk Ways and Lawrence E. Stramm It is certified that error appears in the above-identified patent and that said Letters Patent is hereby corrected as shown below:

In column 4, line 32, after "hydroxy;" insert --$R^3$ is hydrogen, $(CH_2)_m$aryl, $C_1$-$C_4$ alkyl, -COO($C_1$-$C_4$ alkyl), -CONR$^4$R$^5$, -(C=NH)NH$_2$, -SO($C_1$-$C_4$ alkyl), -SO2(NR$^4$R$^5$), or -SO$_2$ ($C_1$-$C_4$ alkyl); $R^4$ and $R^5$ are independently hydrogen, $C_1$-$C_4$ alkyl, phenyl, benzyl, or combine to the nitrogen to which they are bonded to form a saturated or unsaturated 5 or 6 member ring--.

In claim 1, column 12, line 1, delete "and" and insert --$R^3$ is hydrogen, $(CH_2)_m$aryl, $C_1$-$C_4$ alkyl, -COO($C_1$-$C_4$ alkyl), -CONR$^4$R$^5$, -(C=NH)NH$_2$, -SO($C_1$-$C_4$ alkyl), -SO2(NR$^4$R$^5$), or -SO$_2$ ($C_1$-$C_4$ alkyl); $R^4$ and $R^5$ are independently hydrogen, $C_1$-$C_4$ alkyl, phenyl, benzyl, or combine to the nitrogen to which they are bonded to form a saturated or unsaturated 5 or 6 member ring--; in claim 1, column 12, line 2, insert after "AA is an amino acid residue" --m is independently 0, 1, 2, or 3; and n is independently 2, 3, 4, or 5 or a pharmaceutically acceptable salt--; in claim 2, column 12, line 26, after "and m is independently 2 or 3" insert --, or a pharmaceutically acceptable salt--; in claim 3, column 12, line 49, insert after "and m is independently 2 or 3" --, or a pharmaceutically acceptable salt--.

UNITED STATES PATENT AND TRADEMARK OFFICE
CERTIFICATE OF CORRECTION

PATENT NO. : 5,723,456
DATED : March 3, 1998
INVENTOR(S) : Michael R. Jirousek, William Francis Heath, Jr., Douglas Kirk Ways and Lawrence E. Stramm It is certified that error appears in the above-identified patent and that said Letters Patent is hereby corrected as shown below:

In claim 7, column 13, line 34, delete "and" and insert --$R^3$ is hydrogen, $(CH_2)_m$aryl, $C_1$-$C_4$ alkyl, -COO($C_1$-$C_4$ alkyl), -CONR$^4$R$^5$, -(C=NH)NH$_2$, -SO($C_1$-$C_4$ alkyl), -SO2(NR$^4$R$^5$), or -SO$_2$ ($C_1$-$C_4$ alkyl); R$^4$ and R$^5$ are independently hydrogen, $C_1$-$C_4$ alkyl, phenyl, benzyl, or combine to the nitrogen to which they are bonded to form a saturated or unsaturated 5 or 6 member ring--; in claim 7, column 13, line 36, insert after "AA is an amino acid residue" --m is independently 0, 1, 2, or 3; and n is independently 2, 3, 4, or 5 or a pharmaceutically acceptable salt--; in claim 8, column 13, line 62, after "and m is independently 2 or 3" insert --, or a pharmaceutically acceptable salt--.

In claim 9, column 14, line 18, insert after "and m is independently 2 or 3" --, or a pharmaceutically acceptable salt--; in claim 13, column 14, line 62, delete "and" and insert --$R^3$ is hydrogen, $(CH_2)_m$aryl, $C_1$-$C_4$ alkyl, -COO($C_1$-$C_4$ alkyl), -CONR$^4$R$^5$, -(C=NH)NH$_2$, -SO($C_1$-$C_4$ alkyl), -SO2(NR$^4$R$^5$), or -SO$_2$ ($C_1$-$C_4$ alkyl); R$^4$ and R$^5$ are independently hydrogen, $C_1$-$C_4$ alkyl, phenyl, benzyl, or combine to the nitrogen to which they are bonded to form a saturated or unsaturated 5 or 6 member ring--; in claim 13, column 14, line 63, insert after "AA is an amino acid residue" --m is independently 0, 1, 2, or 3; and n is independently 2, 3, 4, or 5 or a pharmaceutically acceptable salt--.

UNITED STATES PATENT AND TRADEMARK OFFICE
CERTIFICATE OF CORRECTION

PATENT NO. : 5,723,456
DATED : March 3, 1998
INVENTOR(S) : Michael R. Jirousek, William Francis Heath, Jr., Douglas Kirk Ways and Lawrence E. Stramm It is certified that error appears in the above-identified patent and that said Letters Patent is hereby corrected as shown below:

In claim 14, column 15, line 20, after "and m is independently 2 or 3" insert --, or a pharmaceutically acceptable salt--; in claim 15, column 15, line 41, insert after "and m is independently 2 or 3" --, or a pharmaceutically acceptable salt--.

In claim 17, column 16, line 12, delete "and" and insert --$R^3$ is hydrogen, $(CH_2)_m$aryl, $C_1$-$C_4$ alkyl, -COO($C_1$-$C_4$ alkyl), -CONR$^4$R$^5$, -(C=NH)NH$_2$, -SO($C_1$-$C_4$ alkyl), -SO2(NR$^4$R$^5$), or -SO$_2$ ($C_1$-$C_4$ alkyl); R$^4$ and R$^5$ are independently hydrogen, $C_1$-$C_4$ alkyl, phenyl, benzyl, or combine to the nitrogen to which they are bonded to form a saturated or unsaturated 5 or 6 member ring--; in claim 17, column 16, line 13, insert after "AA is an amino acid residue" --m is independently 0, 1, 2, or 3; and n is independently 2, 3, 4, or 5 or a pharmaceutically acceptable salt--; in claim 18, column 16, line 36, after "and m is independently 2 or 3" insert --, or a pharmaceutically acceptable salt--; in claim 19, column 16, line 56, insert after "and m is independently 2 or 3" --, or a pharmaceutically acceptable salt--.

UNITED STATES PATENT AND TRADEMARK OFFICE
CERTIFICATE OF CORRECTION

PATENT NO. : 5,723,456
DATED : March 3, 1998
INVENTOR(S) : Michael R. Jirousek, William Francis Heath, Jr., Douglas Kirk Ways and Lawrence E. Stramm It is certified that error appears in the above-identified patent and that said Letters Patent is hereby corrected as shown below:

In claim 22, column 17, line 35, delete "and" and insert --$R^3$ is hydrogen, $(CH_2)_m$aryl, $C_1$-$C_4$ alkyl, -COO($C_1$-$C_4$ alkyl), -CONR$^4$R$^5$, -(C=NH)NH$_2$, -SO($C_1$-$C_4$ alkyl), -SO2(NR$^4$R$^5$), or -SO$_2$ ($C_1$-$C_4$ alkyl); R$^4$ and R$^5$ are independently hydrogen, $C_1$-$C_4$ alkyl, phenyl, benzyl, or combine to the nitrogen to which they are bonded to form a saturated or unsaturated 5 or 6 member ring--; in claim 22, column 17, line 36, insert after "AA is an amino acid residue" --m is independently 0, 1, 2, or 3; and n is independently 2, 3, 4, or 5 or a pharmaceutically acceptable salt--; in claim 23, column 17, line 61, after "and m is independently 2 or 3" insert --, or a pharmaceutically acceptable salt--.

In claim 24, column 18, line 19, insert after "and m is independently 2 or 3" --, or a pharmaceutically acceptable salt--; in claim 26, column 18, line 61, delete "and" and insert --$R^3$ is hydrogen, $(CH_2)_m$aryl, $C_1$-$C_4$ alkyl, -COO($C_1$-$C_4$ alkyl), -CONR$^4$R$^5$, -(C=NH)NH$_2$, -SO($C_1$-$C_4$ alkyl), -SO2(NR$^4$R$^5$), or -SO$_2$ ($C_1$-$C_4$ alkyl); R$^4$ and R$^5$ are independently hydrogen, $C_1$-$C_4$ alkyl, phenyl, benzyl, or combine to the nitrogen to which they are bonded to form a saturated or unsaturated 5 or 6 member ring--; in claim 26, column 18, line 62, insert after "AA is an amino acid residue" --m is independently 0, 1, 2, or 3; and n is independently 2, 3, 4, or 5 or a pharmaceutically acceptable salt--.

UNITED STATES PATENT AND TRADEMARK OFFICE
CERTIFICATE OF CORRECTION

PATENT NO. : 5,723,456
DATED : March 3, 1998
INVENTOR(S) : Michael R. Jirousek, William Francis Heath, Jr., Douglas Kirk Ways and Lawrence E. Stramm It is certified that error appears in the above-identified patent and that said Letters Patent is hereby corrected as shown below:

In claim 27, column 19, line 20, after "and m is independently 2 or 3" insert --, or a pharmaceutically acceptable salt--; in claim 28 column 19, line 41, insert after "and m is independently 2 or 3" --, or a pharmaceutically acceptable salt--.

In claim 30, column 20, line 11, delete "and" and insert --$R^3$ is hydrogen, $(CH_2)_m$aryl, $C_1$-$C_4$ alkyl, -COO($C_1$-$C_4$ alkyl), -CONR'$R^5$, -(C=NH)$NH_2$, -SO($C_1$-$C_4$ alkyl), -SO2(NR'$R^5$), or -$SO_2$ ($C_1$-$C_4$ alkyl); $R^4$ and $R^5$ are independently hydrogen, $C_1$-$C_4$ alkyl, phenyl, benzyl, or combine to the nitrogen to which they are bonded to form a saturated or unsaturated 5 or 6 member ring--; in claim 30, column 20, line 12, insert after "AA is an amino acid residue" --m is independently 0, 1, 2, or 3; and n is independently 2, 3, 4, or 5 or a pharmaceutically acceptable salt--; in claim 31, column 20, line 36, after "and m is independently 2 or 3" insert --, or a pharmaceutically acceptable salt--; in claim 32, column 20, line 56, insert after "and m is independently 2 or 3" --, or a pharmaceutically acceptable salt--.

UNITED STATES PATENT AND TRADEMARK OFFICE
CERTIFICATE OF CORRECTION

PATENT NO. : 5,723,456
DATED : March 3, 1998
INVENTOR(S) : Michael R. Jirousek, William Francis Heath, Jr., Douglas Kirk Ways and Lawrence E. Stramm It is certified that error appears in the above-identified patent and that said Letters Patent is hereby corrected as shown below:

In claim 35, column 21, line 34, delete "and" and insert --$R^3$ is hydrogen, $(CH_2)_m$aryl, $C_1$-$C_4$ alkyl, -COO($C_1$-$C_4$ alkyl), -CONR$^4$R$^5$, -(C=NH)NH$_2$, -SO($C_1$-$C_4$ alkyl), -SO2(NR$^4$R$^5$), or -SO$_2$ ($C_1$-$C_4$ alkyl); R$^4$ and R$^5$ are independently hydrogen, $C_1$-$C_4$ alkyl, phenyl, benzyl, or combine to the nitrogen to which they are bonded to form a saturated or unsaturated 5 or 6 member ring--; in claim 35, column 21, line 35, insert after "AA is an amino acid residue" --m is independently 0, 1, 2, or 3; and n is independently 2, 3, 4, or 5 or a pharmaceutically acceptable salt--; in claim 36, column 21, line 64, after "and m is independently 2 or 3" insert --, or a pharmaceutically acceptable salt--.

In claim 37, column 22, line 22, insert after "and m is independently 2 or 3" --, or a pharmaceutically acceptable salt--; in claim 39, column 22, line 64, delete "and" and insert --$R^3$ is hydrogen, $(CH_2)_m$aryl, $C_1$-$C_4$ alkyl, -COO($C_1$-$C_4$ alkyl), -CONR$^4$R$^5$, -(C=NH)NH$_2$, -SO($C_1$-$C_4$ alkyl), -SO2(NR$^4$R$^5$), or -SO$_2$ ($C_1$-$C_4$ alkyl); R$^4$ and R$^5$ are independently hydrogen, $C_1$-$C_4$ alkyl, phenyl, benzyl, or combine to the nitrogen to which they are bonded to form a saturated or unsaturated 5 or 6 member ring--; in claim 39, column 22, line 65, insert after "AA is an amino acid residue" --m is independently 0, 1, 2, or 3; and n is independently 2, 3, 4, or 5 or a pharmaceutically acceptable salt--.

UNITED STATES PATENT AND TRADEMARK OFFICE
CERTIFICATE OF CORRECTION

PATENT NO. : 5,723,456
DATED : March 3, 1998
INVENTOR(S) : Michael R. Jirousek, William Francis Heath, Jr., Douglas Kirk Ways and Lawrence E. Stramm It is certified that error appears in the above-identified patent and that said Letters Patent is hereby corrected as shown below:

In claim 40, column 23, line 25, after "and m is independently 2 or 3" insert --, or a pharmaceutically acceptable salt--; in claim 41, column 23, line 49, insert after "and m is independently 2 or 3" --, or a pharmaceutically acceptable salt--.

In claim 43, column 24, line 31, delete "and" and insert --$R^3$ is hydrogen, $(CH_2)_m$aryl, $C_1$-$C_4$ alkyl, -COO($C_1$-$C_4$ alkyl), -CONR$^4$R$^5$, -(C=NH)NH$_2$, -SO($C_1$-$C_4$ alkyl), -SO2(NR$^4$R$^5$), or -SO$_2$ ($C_1$-$C_4$ alkyl); R$^4$ and R$^5$ are independently hydrogen, $C_1$-$C_4$ alkyl, phenyl, benzyl, or combine to the nitrogen to which they are bonded to form a saturated or unsaturated 5 or 6 member ring--; in claim 43, column 24, line 32, insert after "AA is an amino acid residue" --m is independently 0, 1, 2, or 3; and n is independently 2, 3, 4, or 5 or a pharmaceutically acceptable salt--; in claim 44, column 24, line 55, after "and m is independently 2 or 3" insert --, or a pharmaceutically acceptable salt--.

In claim 45, column 25, line 18, insert after "and m is independently 2 or 3" --, or a pharmaceutically acceptable salt--.

UNITED STATES PATENT AND TRADEMARK OFFICE
CERTIFICATE OF CORRECTION

PATENT NO. : 5,723,456
DATED : March 3, 1998
INVENTOR(S) : Michael R. Jirousek, William Francis Heath, Jr., Douglas Kirk Ways and Lawrence E. Stramm It is certified that error appears in the above-identified patent and that said Letters Patent is hereby corrected as shown below:

In claim 47, column 26, line 1, delete "and" and insert --$R^3$ is hydrogen, $(CH_2)_m$aryl, $C_1$-$C_4$ alkyl, -COO($C_1$-$C_4$ alkyl), -CONR$^4$R$^5$, -(C=NH)NH$_2$, -SO($C_1$-$C_4$ alkyl), -SO2(NR$^4$R$^5$), or -SO$_2$ ($C_1$-$C_4$ alkyl); R$^4$ and R$^5$ are independently hydrogen, $C_1$-$C_4$ alkyl, phenyl, benzyl, or combine to the nitrogen to which they are bonded to form a saturated or unsaturated 5 or 6 member ring--; in claim 47, column 26, line 2, insert after "AA is an amino acid residue" --m is independently 0, 1, 2, or 3; and n is independently 2, 3, 4, or 5 or a pharmaceutically acceptable salt--; in claim 48, column 26, line 26, after "and m is independently 2 or 3" insert --, or a pharmaceutically acceptable salt--; in claim 49, column 26, line 48, insert after "and m is independently 2 or 3" --, or a pharmaceutically acceptable salt--.

Signed and Sealed this

Twenty-seventh Day of April, 1999

Attest:

*Attesting Officer*

Q. TODD DICKINSON
*Acting Commissioner of Patents and Trademarks*

UNITED STATES PATENT AND TRADEMARK OFFICE
CERTIFICATE OF CORRECTION

PATENT NO. : 5,723,456
DATED : March 3, 1998
INVENTOR(S) : Michael R. Jirousek, William Francis Heath, Jr., Douglas Kirk Ways and Lawrence E Stramm It is certified that error appears in the above-identified patent and that said Letters Patent is hereby corrected as shown below:

Column 4,
Lines 4-14, Formula 1, delete "R" and insert -- $R^1$ --.

Column 11, claim 1,
Lines 41-53, Formula 1, delete "R" and insert -- $R^1$ --.

Column 13, claim 7,
Lines 1-15, Formula 1, delete "R" and insert -- $R^1$ --.

Column 14, claim 13,
Lines 35-37, Formula 1, delete "R" and insert -- $R^1$ --.

Column 15, claim 17,
Lines 50-63, Formula 1, delete "R" and insert -- $R^1$ --.

Column 17, claim 22,
Lines 1-15, Formula 1, delete "R" and insert -- $R^1$ --.

Column 18, claim 26,
Lines 31-44, Formula 1, delete "R" and insert -- $R^1$ --.

Column 19, claim 30,
Lines 51-63, Formula 1, delete "R" and insert -- $R^1$ --.

Column 21, claim 35,
Lines 4-17, Formula 1, delete "R" and insert -- $R^1$ --.

Column 24, claim 43,
Lines 3-15, Formula 1, delete "R" and insert -- $R^1$ --.

UNITED STATES PATENT AND TRADEMARK OFFICE
CERTIFICATE OF CORRECTION

PATENT NO.   : 5,723,456
DATED        : March 3, 1998
INVENTOR(S)  : Michael R. Jirousek, William Francis Heath, Jr., Douglas Kirk Ways and Lawrence E Stramm It is certified that error appears in the above-identified patent and that said Letters Patent is hereby corrected as shown below:

Column 25, claim 47,
Lines 29-41, Formula 1, delete "R" and insert -- $R^1$ --.

Signed and Sealed this

Twentieth Day of November, 2001

Attest:

*Nicholas P. Godici*

NICHOLAS P. GODICI
*Attesting Officer*   *Acting Director of the United States Patent and Trademark Office*